United States Patent [19]

Fugitt et al.

[11] 4,110,473

[45] Aug. 29, 1978

[54] MITICIDAL ETHERS

[75] Inventors: Robert Benson Fugitt, Newark, Del.; Gregory Wayne Schwing, Lincoln University, Pa.

[73] Assignee: E. I. Du Pont de Nemours and Company, Wilmington, Del.

[21] Appl. No.: 815,763

[22] Filed: Jul. 14, 1977

[51] Int. Cl.$^2$ .............................................. A01N 9/24
[52] U.S. Cl. .................................................. 424/331
[58] Field of Search ........................................ 424/331

[56] References Cited

U.S. PATENT DOCUMENTS

| | | | |
|---|---|---|---|
| 2,572,946 | 10/1951 | Paulshock | 424/331 |
| 3,070,492 | 12/1962 | Rapport | 424/331 |

*Primary Examiner*—V. D. Turner

[57] ABSTRACT

Naphthoquinone ethers are useful as miticides having improved knockdown characteristics.

5 Claims, No Drawings

MITICIDAL ETHERS

BACKGROUND OF THE INVENTION

This invention relates to 2-alkyl-1,4-naphthoquinone derivatives which are useful as miticides having improved knockdown characteristics.

C. Beaudit, Helv. Chim. Acta, 30, 1804 (1947) discloses the preparation of 2-methoxy-3-undecyl-1,4-naphthoquinone and states that new derivatives of 2-hydroxy-1,4-naphthoquinone may be of biochemical interest. L. F. Feiser, et al, JACS, 70, 3181 (1948) discloses 2-(3-cyclohexylpropyl)-3-methoxyl-1,4-naphthoquinone, among other naphthoquinone derivatives, which is useful as an antimalarial. However, there is no known reference which teaches that naphthoquinone ethers of this invention would be useful against mites.

SUMMARY OF THE INVENTION

Compounds of the Formula I

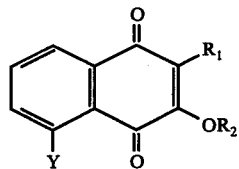

wherein

Y is hydrogen, fluorine, chlorine or bromine;

$R_1$ is alkyl of 8–14 carbon atoms either branched, cyclic, or straight chain;

$R_2$ is saturated alkyl of 1–12 carbon atoms or unsaturated alkyl of 3–12 carbon atoms, either branched or straight chain, optionally substituted with one or two chlorine, bromine, methoxy or ethoxy substituents, or cycloalkyl of 3–6 carbon atoms;

are highly effective against mites and have improved mite knockdown characteristics.

Preferred for their high miticidal activity and favorable cost are those compounds of Formula I wherein Y is hydrogen, $R_1$ is straight chain alkyl of 8–14 carbon atoms, and $R_2$ is saturated alkyl of 2–6 carbon atoms either branched or straight chain.

More preferred for their miticidal activity and economy are those compounds of Formula I wherein independently $R_1$ is straight chain alkyl of 12–14 carbon atoms, and $R_2$ is saturated alkyl of 2–4 carbon atoms either branched or straight chain.

Most preferred for their miticidal activity are those compounds of Formula I where Y is hydrogen or $R_1$ is straight chain alkyl of 12–14 carbon atoms, and $R_2$ is saturated alkyl of 2–4 carbon atoms either branched or straight chain.

Specifically preferred compounds of this invention are 3-ethoxy-2-n-dodecyl-1,4-naphthoquinone and 3-(1-methylethoxy)-2-n-dodecyl-1,4-naphthoquinone.

DETAILED DESCRIPTION OF THE INVENTION

Preparation of the compounds of this invention begins with an appropriate 2-higher alkyl-1-naphthol which can be prepared by the methods taught by K. Nakaniski and L. F. Feiser, J. Amer. Chem. Soc., 74, 3910 (1952) and G. Fawaz and L. F. Feiser, J. Amer. Chem. Soc., 72, 996 (1950). The 2-alkyl-1-naphthol is sulfonated in an inert solvent such as chlorobenzene or methylene chloride. Sulfuric acid and chlorosulfonic acid are satisfactory sulfonating agents.

The product from the sulfonation step, i.e., 2-alkyl-1-naphthol-4-sulfonic acid, is chlorinated in the presence of aqueous ferric chloride to yield a 2-alkyl-3-chloro-1,4-naphthoquinone. The compounds of this invention are prepared from the chloronaphthoquinone by a substitution reaction using an appropriate alcohol in the presence of a suitable base. For example, to produce 3-ethoxy-2-n-dodecyl-1,4-naphthoquinone, the substitution reaction would be carried out using sodium ethoxide in the presence of ethanol. Temperature would preferably be about 25° C. to 80° C. and pressure would be ambient.

Alternatively, the compounds of this invention may be prepared from 2-alkyl-3-hydroxy-1,4-naphthoquinone by an alkylation reaction using an appropriately substituted halohydrocarbon in the presence of a suitable base.

The following examples further illustrate preparation of the compounds of this invention. All parts are by weight and temperatures are in degrees centigrade.

EXAMPLE 1

Preparation of 2-n-dodecyl-1-naphthol-4-sulfonic acid

A solution of 90 parts of sulfuric acid and 670 parts of dichloromethane was added slowly to a solution of 100 parts of 2-n-dodecyl-1-naphthol and 670 parts of dichloromethane at 35°–40° C. After 40 minutes, the mixture was filtered and the precipitate was washed three times with 670 parts of dichloromethane and dried to yield 111 parts of 2-n-dodecyl-1-naphthol-4-sulfonic acid, m.p. 127°–130° C.

EXAMPLE 2

Preparation of 3-chloro-2-n-dodecyl-1,4-naphthoquinone

A mixture of 6.3 parts of 2-n-dodecyl-1-naphthol-4-sulfonic acid, 100 parts of acetic acid, 18 parts of water, 21 parts of sulfuric acid, and 1 part of ferric chloride hexahydrate was cooled to 20° C. Chlorine (3.1 parts) was added to this mixture with vigorous stirring. The temperature rose to 35° C. and the mixture turned yellow. The mixture was heated to 95° C. over 15 minutes and the temperature of the reaction mixture was maintained at 95° C. to 100° C. for 1 hour. Thirty parts of water were added and the mixture was then cooled to 25° C. with vigorous stirring. The crude product, which separated as brown granules, was filtered off and washed three times with water (25 parts), twice with 10% aqueous sodium bicarbonate (25 parts), twice with water (25 parts), twice with cold ethanol (8 parts), and twice with cold hexane (7 parts), to afford 5 parts of 3-chloro-2-n-dodecyl-1,4-naphthoquinone, m.p. 85°–87° C.

EXAMPLE 3

Preparation of 2-n-dodecyl-3-hydroxy-1,4-naphthoquinone

A mixture of 10 parts of 3-chloro-2-n-dodecyl-1,4-napthoquinone, 5 parts of 50% aqueous sodium hydroxide and 320 parts of 95% aqueous ethanol were heated at reflux for 15 minutes. The color of the mixture turned from yellow to dark red. The mixture was cooled to 25° C. and acidified with 10% aqueous hydrochloric acid.

The color of the mixture was golden yellow after acidification. The product was filtered off and washed twice with water (25 parts) and twice with cold methanol (25 parts) to yield 8 parts of 2-n-dodecyl-3-hydroxy-1,4-naphthoquinone, m.p. 85°–87° C.

EXAMPLE 4

Preparation of 2-n-dodecyl-3-ethoxy-1,4-naphthoquinone

Eight parts of 3-chloro-2-n-dodecyl-1,4-naphthoquinone were added in one portion to a solution of 0.54 parts of sodium metal dissolved in 100 parts of ethyl alcohol at ambient temperature. The resulting dark suspension was heated at reflux for two hours. Excess ethyl alcohol was removed in vacuo and the dark residue was recrystallized from 2-propanol to yield 7.6 parts of 2-n-dodecyl-3-ethoxy-1,4-naphthoquinone, m.p. 36°–38° C.

EXAMPLE 5

Preparation of 2-dodecyl-3-methoxy-1,4-naphthoquinone 2.5 parts of anhydrous potassium carbonate and 5 parts of methyl iodide were added in one portion to a solution of 4 parts 2-dodecyl-3-hydroxy-1,4-naphthoquinone in 100 parts N,N-dimethylformamide at ambient temperature. The resulting mixture was stirred overnight, i.e., about 18 hours. The reaction mixture was then poured into about 200 parts of water and the product isolated by filtration. Yield was 3.7 parts 2-dodecyl-3-methoxy-1,4-naphthoquinone, m.p. 66°–67° C.

The following compounds of Table I can be prepared as in Example 4 by substituting the appropriate 2-alkyl-3-chloro-1,4-naphthoquinone for 3-chloro-2-n-dodecyl-1,4-naphthoquinone and the appropriate alcohol for ethanol.

TABLE I

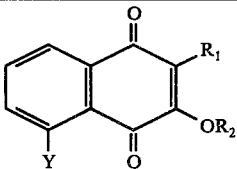

| $R_1$ | Y | $R_2$ |
|---|---|---|
| n-octyl | H | ethyl |
| n-tetradecyl | F | methyl |
| n-tridecyl | Cl | methyl |
| n-dodecyl | H | n-hexyl |
| n-undecyl | H | propen-2-yl |
| n-dodecyl | Br | 1-methylethyl |
| n-dodecyl | H | 1-methylpropyl |
| 1-methyldodecyl | H | cyclopropyl |
| 4-cyclohexylbutyl | H | ethyl |
| n-dodecyl | H | propyn-2-yl |
| n-dodecyl | H | cyclohexyl |
| n-dodecyl | H | butyl |
| 1,2-dimethyldecyl | H | hexen-2-yl |
| n-dodecyl | H | 2-methylpropyl |
| n-dodecyl | H | 2-methoxyethyl |
| n-dodecyl | H | 2-ethoxyethyl |
| n-dodecyl | H | hexyn-3-yl |
| n-dodecyl | H | 6-methoxyhexyl |
| n-dodecyl | H | 1-dodecyl |
| n-dodecyl | H | 2-dodecen-1-yl |
| n-dodecyl | H | 2-dodecyn-1-yl |

The following compounds of Table II are prepared as in Example 5 by substituting the appropriate 2-alkyl-3-hydroxy-1,4-naphthoquinone for 2-n-dodecyl-3-hydroxy-1,4-naphthoquinone and the appropriate alkyl, alkenyl, alkynyl, iodide or bromide for methyl iodide.

TABLE II

| $R_1$ | Y | $R_2$ |
|---|---|---|
| n-dodecyl | H | 2-chloroethyl |
| n-dodecyl | H | 4-chlorobuten-2-yl |
| n-dodecyl | H | 6-bromohexyn-3-yl |
| n-dodecyl | H | 2,2-dichloroethyl |
| tetradecyl | H | 2-bromo-2,2-dimethylethyl |

The compounds represented by Formula I provide excellent control of plant-feeding mites. They are especially useful for control of those species which attack fruit trees, nut trees, grain and seed crops, field and vegetable crops and ornamentals. Apple trees, hops, roses, peach trees, strawberries, almonds, tobacco, corn, cotton, citrus, beans and peanuts are particularly susceptible to mite damage and can be protected by application of the compounds of this invention.

Among the species of mites controlled by the compounds of this invention are: *Tetranychus urticae*, two-spotted mite; *Panonychus ulmi*, European red mite; *Tetranychus atlanticus*, strawberry spider mite; *T. cinnabarinus*, carmine spider mite; *T. pacificus*, Pacific mite; *Panonychus citri*, citrus red mite; *Bryobia praetiosa*, clover mite; *Aceria neocynodomis*, grass mite; *Bryobia rubrioculus*, brown mite; *Aceria sheldoni*, citrus bud mite; *Steneotarsonemus pallidus*, cyclamen mite; *Tetranychus mcdanieli*, McDaniel mite; *T. schoenei*, Schoene mite; and *Oligonychus pratensis*, Banks grass mite.

Mites contacting compounds of Formula I either directly from sprays or indirectly by walking over treated surfaces are rapidly affected or are killed if they have been exposed to a sufficiently high dosage. The quantity of compound needed for mite control will vary depending upon the specific situation. Factors affecting mite control are: the type of crop, the stage of development of the crop, the volume of spray applied, the interval between applications, the species of mite to be controlled, its population dynamics, temperature, amount and frequency of rainfall, the intensity of sunlight, etc. For plant protection applications of the active ingredients may be made from either dilute or concentrated media. Many growers prefer to make high-volume applications with tractor-drawn ground equipment. They enjoy the benefits of the excellent leaf coverage inherent in the use of this method. Other growers prefer low-volume applications made by aircraft due to the economy and rapid treatment afforded by this method.

The concentration of active ingredient in the medium (usually aqueous) actually applied will vary with the method used. In high-volume field applications quantities of from 20–4000 ppm are generally useful. Preferred are concentrations containing 40–2000 ppm, and most preferred are those containing 80–500 ppm. In low-volume applications liquid concentrates as described elsewhere in this specification may be applied directly using appropriate metering devices and nozzles. Alternatively, these can be diluted to provide any desired volume of spray per hectare that is most effective under the prevailing circumstances. On an area basis, in general, 0.02–16 kilograms of active ingredient per hectare are sufficient, preferably 0.05–8 kilograms and most preferably 0.14–4 kilograms. To assure control throughout the growing season, multiple applications at desired intervals may be utilized.

It may be desirable or useful to mix the compounds of this invention with other agricultural pesticides, superior oil or adjuvants. Such mixtures often increase the effectiveness of the application on mites and broaden the scope of control to embrace other pests such as insects, fungi, nematodes, or bacteria. Other pesticides with which the compounds of this invention may be mixed to achieve broader-spectrum activity include:

diazinon—O,O-diethyl-O-(2-isopropyl-4-methyl-6-pyrimidyl)phosphorothioate
disulfoton—O,O-diethyl S-2-(ethylthio)-ethylphosphorodithioate
azinphosmethyl—O,O-dimethyl S-[4-oxo-1,2,3-benzotriazin-3 (4H)ylmethyl]-phosphorodithioate
phorate—O,O-diethyl S-(ethylthio)methylphosphorodithioate
oxamyl—S-methyl 1-(dimethylcarbamoyl)-N-[methylcarbamoyl)]thioformimidate
methomyl—S-methyl N-(methylcarbamoyloxy)-thioacetimidate
benomyl—1-butylcarbamoyl-2-benzimidazolecarbamic acid, methyl ester
captan—N-trichloromethylthiophthalimide
maneb—ethylenebisdithiocarbamic acid, manganese salt
dodine—n-dodecylguanidine acetate
folpet—N-(trichloromethylthio)phthalimide
captafol—cis-N-[(1,1,2,2-tetrachloroethyl)-thio]-4-cyclohexene-1,2-dicarboximide
carboxin—5,6-dihydro-2-methyl-1,4-oxathiin-3-carboxanilide
streptomycin—2,4-diguanidino-3,5,6-trihydroxycyclohexyl-5-deoxy-2-o-(2-deoxy-2-methylamino-α-glycopyranosyl)-3-formylpentofuranoside
NRDC-143—m-phenoxybenzyl cis,trans-($\pm$)-3-(2,2-dichlorovinyl)-2,2-dimethylcyclopropane-carboxylate
— —2-acetoxy-3-m-dodecyl-1,4-naphthoquinone
BAY NTN 9306—O-ethyl O[4-(methylthio)phyenyl] S-propyl phosphorodithioate
CGA-15324—(O-4-bromo-2-chlorophenyl)0-ethyl S-propylphosphorothioate
NRDC-143 Permethrin—m-phenoxybenzyl cis,trans-($\pm$)-3-(2,2-dichlorovinyl)-2,2-dimethylcyclopropane carboxylate
SD-43775—benzeneacetic acid, 4-chloroalpha-(1-methylethyl)-cyano(3-phenoxyphenyl) methyl ester
EPN—ethyl p-nitrophenylthiobenzene phosphonate
polynactin complex—Structure of polynactin complex (tetranactin, trinactin and dinactin)
    tetranactin: $R_1, R_2, R_3, R_4$ = ethyl
    trinactin: $R_1, R_2, R_3$ = ethyl, $R_4$ = methyl
    dinactin: $R_1, R_3$ = ethyl, $R_2, R_4$ = methyl

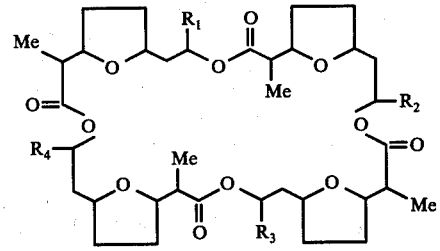

The miticidal activity of the compounds of this invention is further illustrated by the following examples.

EXAMPLE 6

Bean plants in the two-leaf stage were infested with 50-100 two-spotted spider mites, *Tetranychus urticae* Koch, per leaf and sprayed to run-off with aqueous suspensions of the compounds of this invention. These were made by dissolving appropriate quantities of the miticidal ethers listed below in 5 ml of acetone and diluting the mixture to the desired spray concentration with water containing Surfactant F (Trem 014) at 1:3000. After spraying, the plants were held under greenhouse conditions for two days. Percent mite mortality was determined at this time.

The results are recorded in the table below:

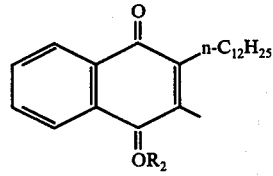

| $R_2$ | % Mite Mortality 2-Day | |
|---|---|---|
| | 100 ppm | 50 ppm |
| —CH$_3$ | 100 | 100 |
| —CH$_2$CH$_3$ | 100 (100)[1] | 99 (100) |
| —CH(CH$_3$)$_2$ | 100 | 97 |
| —CH$_2$CH$_2$CH$_3$ | 100 | 98 |
| —(CH$_2$)$_3$CH$_3$ | 100 | 98 |
| —CH(CH$_3$)CH$_2$CH$_3$ | 100 | 98 |
| —(CH$_2$)$_2$CH(CH$_3$)$_2$ | 100 | 98 |
| —C$_8$H$_{17}$ | 100 | 99 |
| CH$_2$CH=CH$_2$ | 100 | 100 |

[1] Number is parenthesis from a second test.

EXAMPLE 7

Results for an experiment, similar in all respects to that described in Example 6, with the exception that percent mite mortality was determined at the end of one week.

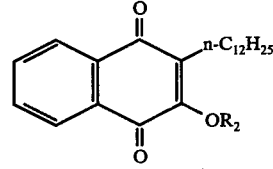

| $R_2$ = | % Mite Mortality 7-Day | |
|---|---|---|
| | 100 ppm | 50 ppm |
| —CH$_2$CH$_3$ | 100 | 100 |
| —CH$_2$CH$_2$CH$_3$ | 100 | 100 |
| —CH(CH$_3$)CH$_2$CH$_3$ | 99 | 100 |
| —(CH$_2$)$_2$CH(CH$_3$)$_2$ | 100 | 100 |

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al, "Handbook of Insecticide Dust Diluents and Carriers", 2nd, Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

Compositions containing the compounds of Formula I as active ingredient are further illustrated by the following examples.

EXAMPLE 8

Emulsifiable Concentrate 3-ethoxy-2-n-dodecyl-1,4-naphthoquinone: 20%
chlorobenzene: 74%
sorbitan monostearate and polyoxyethylene condensates thereof: 6%

The ingredients are combined and stirred to produce a solution which can be emulsified in water for application.

EXAMPLE 9

Emulsifiable Concentrate 3-(1-methylethoxy)-2-n-dodecyl-1,4-naphthoquinone: 30%
blend of oil soluble sulfonates and polyoxyethylene ethers: 4%
xylene: 66%

The ingredients are combined and stirred with gentle warming to speed solution. A fine screen filter is included in the packaging operation to insure the absence of any extraneous undissolved material in the product.

EXAMPLE 10

WETTABLE POWDER 3-(1-methylethoxy)-2-n-dodecyl-1,4-naphthoquinone: 65%
dodecylphenol polyethylene glycol ether: 2%
sodium ligninsulfonate: 4%
sodium silicoaluminate: 6%
montmorillonite (calcined): 23%

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 11

Wettable Powder 3-ethoxy-2-n-dodecyl-1,4-naphthoquinone: 40%
dioctyl sodium sulfosuccinate: 1.5%
sodium ligninsulfonate: 3%
low viscosity methyl cellulose: 1.5%
attapulgite: 54%

The ingredients are thoroughly blended, passed through an air mill, to produce an average particle size under 15 microns, reblended, and sifted through a U.S.S. No. 50 sieve (0.3 mm opening) before packaging.

EXAMPLE 12

Granule 3-ethoxy-2-n-dodecyl-1,4-naphthoquinone: 10%
attapulgite granules (low volatile matter, 0.71/0.30 mm; U.S.S. No. 25-50 sieves): 90%

The active ingredient is warmed to approximately 90° C. and sprayed upon dedusted and prewarmed attapulgite granules in a double cone blender. The granules are then allowed to cool and are packaged.

All compounds of this invention may be formulated in the same manner.

What is claimed is:

1. A method for protecting plants from mites which comprises applying to the plant a miticidally effective amount of a compound of the Formula I

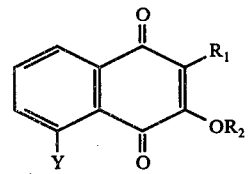

wherein Y is hydrogen, fluorine, chlorine, or bromine;
$R_1$ is alkyl of 8–14 carbon atoms either branched, cyclic, or straight chain;
$R_2$ is saturated alkyl of 1–12 carbon atoms or unsaturated alkyl of 3–12 carbon atoms either branched or straight chain, optionally substituted with one or two chlorine, bromine, methoxy or ethoxy substituents, or cycloalkyl of 3–6 carbon atoms.

2. The method of claim 1 wherein $R_1$ is straight chain alkyl of 8–14 carbon atoms, $R_2$ is saturated alkyl of 2–6 carbon atoms either branched or straight chain and Y is hydrogen.

3. The method of claim 1 wherein Y is hydrogen, $R_1$ is straight chain alkyl of 12–14 atoms, and $R_2$ is saturated alkyl of 2–4 carbon atoms either branched or straight chain.

4. The method of claim 1 in which the compound is 3-ethoxy-2-n-dodecyl-1,4-naphthoquinone.

5. The method of claim 1 in which the compound is 3-(1-methylethoxy)-2-n-dodecyl-1,4-naphthoquinone.

* * * * *